United States Patent [19]

Kreuter et al.

[11] Patent Number: 5,906,848

[45] Date of Patent: *May 25, 1999

[54] PROCESS FOR THE REMOVAL OF UNDESIRED CONTAMINATIONS AND/OR RESIDUES CONTAINED IN BEVERAGES OR IN VEGETABLE PREPARATION

[75] Inventors: Mathias-Heinrich Kreuter, Walenstadt; Rudolf Steiner, Bäch, both of Switzerland

[73] Assignee: Emil Flachsmann AG, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/611,687

[22] Filed: Mar. 6, 1996

[30] Foreign Application Priority Data

Mar. 6, 1995 [CH] Switzerland .............................. 0629/95
Jun. 2, 1995 [CH] Switzerland .............................. 1621/95

[51] Int. Cl.$^6$ ................................ A23D 9/00; A23D 3/20
[52] U.S. Cl. ........................ 426/330; 426/429; 426/486; 426/417; 426/590; 554/8
[58] Field of Search ................................ 426/486, 487, 426/488, 424, 330, 330.6, 425, 426, 429, 430, 417, 599; 554/8

[56] References Cited

U.S. PATENT DOCUMENTS

| | | | |
|---|---|---|---|
| 2,815,287 | 12/1957 | Barnett | 426/430 |
| 2,934,432 | 4/1960 | King | 426/430 |
| 3,723,410 | 3/1973 | Persinos | 426/425 |
| 3,914,454 | 10/1975 | Takatsu | 426/309 |
| 3,955,004 | 5/1976 | Strauss | 426/488 |
| 4,009,290 | 2/1977 | Okumou | 426/489 |
| 4,032,551 | 6/1977 | Willett | 426/430 |
| 4,055,674 | 10/1977 | Yano | 426/430 |
| 4,062,984 | 12/1977 | Lindquist | 426/430 |
| 4,069,351 | 1/1978 | Yano | 426/429 |
| 4,072,671 | 2/1978 | Sodini | 426/430 |
| 4,084,007 | 4/1978 | Hepp | 426/430 |
| 4,104,290 | 8/1978 | Koslowsky | 429/429 |
| 4,126,709 | 11/1978 | Johnson | 426/489 |
| 4,148,928 | 4/1979 | Sodini | 426/430 |
| 4,201,709 | 5/1980 | Kadan | 426/430 |
| 4,377,600 | 3/1983 | Morinaga . | |
| 4,780,279 | 10/1988 | Enos | 426/320 |
| 4,804,555 | 2/1989 | Marschner | 426/488 |
| 4,874,629 | 10/1989 | Chang | 426/487 |
| 4,956,429 | 9/1990 | Harmetz | 426/429 |
| 4,968,518 | 11/1990 | Lopez | 426/330.6 |
| 5,023,100 | 6/1991 | Chang | 426/487 |
| 5,079,019 | 1/1992 | Hirshbrunner | 426/429 |
| 5,094,868 | 3/1992 | Wolfram | 426/460 |
| 5,312,635 | 5/1994 | Kazlas | 426/417 |
| 5,358,732 | 10/1994 | Seifter | 426/487 |
| 5,468,511 | 11/1995 | Zeidler | 426/429 |
| 5,470,601 | 11/1995 | Robertson | 426/429 |
| 5,558,893 | 9/1996 | Muraldihara | 426/492 |
| 5,676,991 | 10/1997 | Dull | 426/425 |

FOREIGN PATENT DOCUMENTS

| | | |
|---|---|---|
| 0013659 | 7/1980 | European Pat. Off. . |
| 0080298 | 6/1983 | European Pat. Off. . |
| 0382116 | 8/1990 | European Pat. Off. . |
| 2220292 | 10/1974 | France . |
| 1289400 | 2/1969 | Germany . |
| 714904 | 9/1954 | United Kingdom . |
| WO01118 | 4/1982 | WIPO . |

*Primary Examiner*—Carolyn Paden
*Attorney, Agent, or Firm*—Burns, Doane, Swecker & Mathis, L.L.P.

[57] ABSTRACT

A process for the removal of undesired lipophilic contaminations and/or residues, which are contained in beverages or in vegetable preparations. The process comprises a first step in which a beverage or vegetable preparation is mixed with a lipophilic phase such that the contaminations and/or residues to be removed are dissolved in the lipophilic phase and are concentrated therein nearly quantitatively. In a second step, the lipophilic phase, which contains the contaminations and/or residues, is separated from the beverage or vegetable preparation. Finally, the purified beverage or vegetable preparation is obtained.

5 Claims, No Drawings

PROCESS FOR THE REMOVAL OF UNDESIRED CONTAMINATIONS AND/OR RESIDUES CONTAINED IN BEVERAGES OR IN VEGETABLE PREPARATION

BACKGROUND OF THE INVENTION

The present invention is directed to a process for the removal of undesired lipophilic contaminations and/or residues, which are contained in beverages or in vegetable preparations.

Organic lipophilic compounds have been used for decades as plant protective products, pest control compounds and pesticides.

Some of these highly active toxic substances have the undesired characteristic that they are degraded after accumulation in lipophilic parts of plants either only insufficiently or are not degraded at all.

It is known, that the plant protective compound pentachloro nitrobenzene is transformed in the degradation products pentachloro aniline, pentachloro anisol and pentachloro benzene.

These degradation products are also toxic.

Said highly active toxic compounds, which are degraded only insufficiently or are not degraded at all, are thus accumulated in the soil, in the water and in the human body or in the bodies of animals, combined with corresponding negative effects.

Thus, the whole food chain, the end of which is the human being, is poisonned.

Due to these reasons the use of certain active compounds, such as DDT and lindan, has been strongly restricted or forbidden.

The use of supercritical carbon dioxide ($CO_2$) is only applicable to a restricted extent for the removal of these undesired highly active toxic substances; see for example EP PS 0 382 116 B1.

Contaminated water may be purified by using active carbon.

This purification process is very expensive and is not selective.

Lipophilic contaminations, especially lipophilic poisons of the above mentioned kind, may be removed with halogenated hydrocarbons, such as methylene chloride, chloroform, carbon tetrachloride, or with alkanes containing 5 to 7 carbon atoms, such as petroleum ether, hexane.

But these substances for removing of the lipophilic poisons of said kind are themselves toxic, detrimental to the environment and to some extent highly explosive, whereby their use is combined with high risks.

Various national and international laws and implementing regulations have been promulgated, wherein maximum amounts of poisons are defined.

It is an object of the present invention to provide a process with which these highly active toxic ompounds may be removed nearly quantitative and selectively from beverages or vegetable preparations.

This process is also be cheap as well as simple and safe during realization.

In this process no toxic and/or easy inflammable agents are used.

This process has no drawbacks for the environment.

With this process the maximum amounts of poisons as defined in national and international laws and implementing regulations shall be at least accomplished and preferably will be significant below these amounts.

The inventive process meets the above mentioned objects.

SUMMARY OF THE INVENTION

The inventive process for the removal of undesired lipophilic contaminations and/or residues, which are contained in beverages or in vegetable preparations, is characterized in that in a first step the corresponding beverage or the corresponding vegetable preparation is mixed with such a lipophilic phase, that the contaminations and/or residues to be removed are dissolved in this lipophilic phase and are concentrated herein nearly quantitatively, in a second step the liphophilic phase, which contains now the contaminations and/or residues, is separated from the corresponding beverage or from the corresponding vegetable preparation, and in a third step the so purified beverage or so purified vegetable preparation is obtained.

DETAILED DESCRIPTION OF THE PREFERRED EMBODIMENTS

According to the invention, the lipophilic contaminations and/or residues can be pesticides, plant protective products, pest control agents, especially fungicides, insecticides, acaricides, nematicides, herbicides, or environmental poisons, such as polyhalogenated, especially polychlorinated, biphenyls, dioxines, or organic solvents, such as benzene, chloroform, carbon tetrachloride, or synthesis residues, such as alkylhalides, halogenated aromatic substances and heteroatomic aromatic substances, such as chloropyridines, including any mixtures thereof.

More particularly, the lipophilic contaminations and/or residues can be:

α—hexachloro cyclohexane,

β—hexachloro cyclohexane,,

γ—hexacholoro cyclohexane, also named lindan,

δ—hexachloro cyclohexane, pentachloro nitrobenzene, also named quintozen, and its degradation products, such as pentachloro aniline, pentachloro anisol, pentachloro benzene, dichloro-diphenyl-trichloro-ethane, also named DDT, and its degradation products, such as dichloro-di-phenyl-dichloro-ethylene, also named DDE, endosulfan, also named thiodan, pyrethrum and its synergists, piperonylbutoxide, hexachloro benzene, aldrin, dieldrin, heptachlor, and methoxychlor.

Beverages which may be treated according to the invention may include drinking water, table-water, mineral water, wine, beer, fruit-juices, tea or lemonades.

Vegetable preparations which may be treated according to the invention may include infusions, tinctures, fluids, spissum extracts, siccum extracts, dropping solutions, juices, tonics, or injectable preparations.

The vegetable preparations can be partial or complete extracts from medical and/or spice plants or parts thereof, especially:

*Abelmoschus moschatus L* (Semen);
*Acorus calamus* (Rhizom);
*Aesculus hippocastanum L.* (Semen);
Allium-species (e.g. *A. cepa L., A. ursinum L., A. sativum L.*:Bulbus);
*Alpinia officinarum Hance* (Rhizom);
*Anethum graveolens L.* (Fructus);
*Angelica archangelica L.*, various subspec. (Rhizoma);

*Angelica dahurica* (Radix);
*Angelica formosana* (Radix);
*Anthemis nobilis L.* (Chamomilla romana, Herba);
*Apium graveolens L.* (Fructus);
*Arctium major Gaertn.* (Radix);
*Arctostaphylos uvaursi Spreng.* (Folium);
*Arnica montana L.* (Flos);
*Artemisia absinthium L.* (Herba);
*Artemisia dracunculus L.* (Herba);
*Asparagus offic.* (Herba, Rhizoma, Radix);
*Atropa belladonna L.* (Folium);
*Berberis vulgaris L.* (Cortex, Radix);
Betula-species (Folium);
*Brassica nigra* (L.) Koch (Semen);
*Camellia sinensis* (Folia);
*Carum carvi L.* (Ftudtus);
*Cetraria islandica* (L.) Ach.;
*Chrysanthemum vulgare Asch.* (Herba);
Cinnamomum-species (Cortex);
Citrus-species (Folium, Flavedo, Fruct.);
*Copaifera reticulate Ducke* (Balsam);
*Coriandrum sativum L.* (Fructus);
*Cucurbita pepo L.* (Semen);
*Cuminum cyminum L.* (Fructus);
Curcuma-species (Rhizoma);
*Cusparia officinalis* (Willd.) Eng. (Cortex);
*Dipterocarpus turbinatus Gaertn.* (Balsamum);
Drosera species (*D. rotundifolia L., D.ramentacea Burch*; Herba);
*Echinacea angustifolia D.C.* (Radix);
*Echinacea purpurea* (L.) Moench (Radix);
*Elettaria cardamonum* (L.) White et Mathon (Fructus);
*Equisetum arvense L.* (Herba);
*Eucalyptus globulus Labill.* (Folium);
*Fagopyrum vulgare Hill.* (Herba);
*Foeniculum vulgare Miller* (Fructus);
*Fumaria offic.* (Herba);
*Gaultheria procumbens L.* (Folium);
*Ginkgo biloba L.* (Folium);
*Hamamelis virginiana L.* (Cortex, Folium);
*Hedeoma pulegioides* (L.) Pers. (Herba);
*Herniaria glabra L.* (Herba);
*Humulus lupulus L.* (Flos, Glandulae);
*Hypericum perforatum L.* (Herba);
*Hysopus officinalis L.* (Herba);
*Ilex paraguariensis St. Hil.* (Folium mate);
*Illicium verum Hook. f.* (Fructus);
*Iluna helenium L.* (Rhizoma);
*Iris pallida Lam.* (Rhizoma);
*Jasminum grandiflorum L.* (Flos);
*Laurus nobilis L.* (Folium, Fructus);
*Lavendtla officinalis,* further species (Flos);
*Lawsonia inermis L.* (Folium);
*Levisticum officinale Koch* (Radix);
Melaleuca: various varieties (Folium);
*Matricaria chamomilla L.* (Flos);
*Melilotus officinalis* (L.);
*Lam. em. Thuill.* (Herba);
*Melissa officinalis L.* (Herba);
Mentha-species and its varieties (Folium);
*Myristica fragrans Houttuyn* (Arillus, Semen);
*Myrtus communis L.* (Folium);
*Ocimum basilicum L.* (Herba);
*Ocotea sassafras* (Cortex);
*Oenanthe aquatica* (L.) Poir (Fructus);
*Olea europaea* (Folia);
Olibanum (Resinum);
*Ononis spinosa L.* (Radix);
Origanum-species (Herba);
*Orthosiphon stamineus Benth.* (Herba);
*Panax ginseng Meyer* (Radix);
*Petroselinum crispum* (Mill.) Nym. (Fructus, Herba);
*Phaseolus vulgaris L.* (Fructus sine Semine);
*Pimenta dioica* (L.) Merill (Fructus);
*Pimpinella anisum L.* (Semen);
*Piper angustifolium Ruiz. et Pavon.* (Folium);
*Piper methysticum Forster* (Radix);
*Pogostemon patchouli Pell.* (Folium);
*Prunus laurocerasus L.* (Folium);
*Rhus aromatics Ait.* (Cortex);
*Rosmnarinus officinalis L.* and its species (Folium);
*Rubia tinctorum L.* (Radix);
*Rubus fructicosus L.* (Folium);
*Ruta graveolens L.* (Herba);
*Sabal serulata Benth et Hook* (Fructus);
*Salix alba L.* (Cortex) and all species thereof;
Salvia-species (Folium);
*Santalum album L.* (Liqnum);
*Sarothamnus scoparius* (L.) Wimmer (Herba);
*Sassafras albidum* (Nutt.) Nees (Liqnum);
*Satureja hortensis L.* (Herba);
*Scopolia carniolica Jacq.* (Radix);
*Solidago serotina Ait.* (Herba);
*Solidago virgaurea L.* (Herba);
*Syzyqium aromaticum Merr.* et Perry (Flores, Folium);
*Taraxacum of ficinale Web.* (Herba and Radix);
*Thymus serpyllum L.* (Herba);
*Thymus vulgaris L.* Herba;
*Tilia cordata Mill.* and *T. platyphyllos Scop.* (Flos);
*Urtica dioica L.* (Folium, Radix);
*Valeriana officinalis* and its varieties (Radix);
*Vitis vinifera* (Folia); and
Zingiberis officinale Roscoe(Rhizoma).

The vegetable preparations can be partial or complete extracts from alkaloids and/or flavonoides and/or saponines and/or bitterings and/or terpenes containing plants or parts thereof selected from: Betulae (Folia); Boldo (Folia); Camelliae (Folia); Chelidonii (Herba); Chinae (Cortex); Chrysanthemi (Herba); Crataegi (Folia c. Floribus); Cynarae (Folia); Gentianae (Radix); Ginkgo (Folia); Ginseng (Radix); Hederae helic. (Herba); Hippocastani (Semen); Liquiritiae (Radix); Orthosiphonis (Folia); Passiflorae (Herba); Rauwolfiae (Radix); Salicis (Cortex); Solidaginis (Herba); Tiliae (Flores); and *Vitis vinifera* (Folia, Fructus).

The liphophilic phase can be of animal, vegetable, mineralic or synthetic origin, and is especially not toxic, not easily inflammable, not explosive and not volatile, and is preferably selected from:

fats, such as cocoa butter, coconut fat;
oils, such as neutral oils, sunflower oil, fractionated coconut oil, such as miglyol;
waxes, such as stearins, yoyoba oil, beeswax, spermaceti, carnauba wax;
paraffins, including vaseline;
lipoids; and
sterols. All of the aforementioned compounds, as simple compounds or as mixtures, preferably fulfill the requirements/definitions in the "Deutsches Arzneibuch, DAB", or in the British Pharmacopoe, BP, or according to the Food Chemical Codex, FCC, in the United States of America, or must correspond to these requirements/definitions, respectively.

According to the process of the invention, in the first step the mixing of the components is conducted at such a temperature, which lies between the freezing point and the boiling point of the respective mixture, whereby a temperature in the range from room temperature to 70° C. is preferred.

In the first step of the process, the components can be mixed together for about 1 hour, preferably using means of shaking or stirring. In the second step the separation is preferably conducted either by means of a phase separation of 2 liquid phases or by means of a phase separation of a liquid phase and a solid phase. In the second step the separation of 2 liquid phases is preferably conducted by membrane-separation, using glass-, metal-, ceramic- and synthetic membranes with pore sizes in the range from 0.001 to 1.0 micrometers, more preferably from 0.1 to 0.3 micrometers. Preferred synthetic membranes are those made of polypropylene or teflon.

In the process according to the invention separated lipophilic phase, containing the contaminations and/or residues, can be subjected to a water vapor distillation, and the obtained distillate, which contains lipophilic, volatile-in-steam smell components and/or taste components, can be added back as such or after previous removal of the water to the purified beverage or purified vegetable preparation (at the end of the third step).

For vegetable preparations, which contain alkaloids, at least one physiologically acceptable acid can be added during the mixing step in such a way and in such an amount to adjust the pH to a level whereby the alkaloids are present as salts. Examples of such acids include ascorbic acid, citric acid, acetic acid.

In the second step of the inventive process a separation of two phases is carried out.

Thereby either two liquid phases of a liquid phase and a solid phase are separated.

When two liquid phases are separated from each other, then this is realized preferably by means of membrane technology.

Thereby tubular membranes, so called "cross-flow"-membranes, are preferred.

Thereby the used membrane is preferably conditioned previously.

When it is desired, that the hydrophilic phase is obtained as filtrate and the lipophilic phase as retentate, then the membrane is conditioned at room temperature with a hydrophilic solvent, especially water, or with a hydrophilic mixture of solvents, for example a mixture of 85 vol.-% water and 15 vol.-% ethanol, for a few minutes, for example 5 to 20 minutes, especially 10 minutes.

In principle it is also possible to condition the membrane with the hydrophilic phase itself.

When it is desired, that the lipophilic phase is obtained as filtrate and the hydrophilic phase as retentate, then the membrane, in analogy to the above mentioned statements, is conditioned with a lipophilic solvent or a mixture of solvents or with the lipophilic phase itself.

It is preferred to obtain the hydrophilic phase as filtrate.

After this conditioning of the membrane the mixture to be separated, for example 9 parts hydrophilic preparation and 1 part lipophilic phase, is subjected to the above mentioned continuous membrane separation during such a long time until the desired amount of the purified hydrophilic preparation is obtained as filtrate.

When a liquid phase and a solid phase are separated from each other, then this is realized by means of conventional technology.

In this case cocoa butter is preferred as lipophilic phase.

Thereby cocoa butter in a molten state is stirred in into the hydrophilic preparation to be purified, and which phase has preferably a temperature of about 50° C.

This mixture is stirred during about 1 hour at a temperature of about 50° C.

Then the mixture is allowed to cool to room temperature or to a temperature in the range from 5° C. to 10° C., especially 8° C.

At these temperatures the cocoa butter becomes solid and may be separated from the purified hydrophilic preparation.

In the inventive process during the extraction step both the hydrophilic phase and the lipophilic phase are preferably each in a liquid state of aggregation.

The following examples illustrate the present invention.

EXAMPLE 1

400 g of Extr. Ginseng e. rad. spir. spiss. were mixed with 800 g of distilled water and were brought under stirring to a temperature of 50° C.

After reaching the temperature 40 g of cocoa butter in molten state were added under stirring, and this mixture was stirred during 1 hour at a temperature of 50° C.

Then the mixutre was stored for 2 days at 8° C.

Then the solid mass, which contained cocoa butter and the contaminations, and which mass was at the surface of the mixture was left off and thrown away.

The residue, that is the liquid extract solution, was filtered through a folded filter.

The obtained filtrate was concentrated under vacuum at a temperature of 50° C. in maximum to the starting weight of 400 g.

The pesticide values of the so obtained product are mentioned in table 1.

EXAMPLE 2

1000 g of extract ginseng e. rad. spir. spiss. were mixed with 4000 g of distilled water and were brought under stirring to a temperature of 50° C.

After reaching the temperature 100 g of cocoa butter in molten state were added under stirring, and this mixture was stirred during 1 hour at a temperature of 50° C.

The mixture was then cooled to 30° C. and was filtered by means of closs-flow in an ultra filtration device during 2 hours.

The membrane (polypropylene-tube module) of the cross-flow-device was conditioned previously during 10 minutes with distilled water, which had a temperature from 30° C. to 42° C.

The obtained filtrate was concentrated at a temperature of 50° C. in maximum to the starting weight of 1000 g.

The pesticide values of the so obtained product are mentioned in table 1.

EXAMPLE 3

500 g extract Ginseng e. rad. spir. spiss. were mixed with 2000 g of distilled water and were stirred during 15 minutes at a temperature of 50° C.

Then were added 50 g of miglyol 812, and it was stirred for a further hour at a temperature of 50° C.

This mixture was allowed to stand over night at room temperature.

Then this mixture was filtered by means of cross-flow in an ultra filtration device during 1 hour.

The membrane (polypropylene-tube module) of the cross-flow-device was conditioned previously during 10 minutes with distilled water at room temperature.

The obtained filtrate was concentrated at a temperature of 50° C. in maximum to the starting weight of 500 g.

The pesticide values of the so obtained product are mentioned in table 1.

TABLE 1

|  | Values in the starting material (in ppm) | values in the treated material (in ppm) | | |
| --- | --- | --- | --- | --- |
|  |  | example 1 | example 2 | example 3 |
| α-HCH *) | <0.020 | <0.010 | <0.010 | <0.010 |
| γ-HCH | 0.038 | 0.011 | <0.010 | <0.010 |
| β-HCH | 0.0760 | <0.010 | <0.010 | <0.010 |
| δ-HCH | 0.700 | 0.130 | 0.035 | 0.025 |
| Pentachloro benzene | <0.100 | <0.100 | <0.100 | <0.100 |
| Pentachloro anisol | <0.100 | <0.100 | <0.100 | <0.100 |
| Pentachloro aniline | 1.66 | 0.360 | 0.130 | 0.130 |
| Quintozen | <0.02 | 0.012 | <0.010 | <0.010 |

*) HCH: Hexachloro cyclohexane

We claim:

1. A process for the removal of at least one undesired lipophilic contamination or residue, which is contained in beverages or in vegetable preparations, comprising:
   in a first step mixing the beverage or the vegetable preparation with a lipophilic phase to dissolve in this lipophilic phase and concentrate therein nearly quantitatively the contamination or residue, and wherein the lipophilic phase is of animal, vegetable, mineralic or synthetic origin, and is not toxic, not easily inflammable, not explosive and not volatile,
   in a second step separating the lipophilic phase, which contains the at least one contamination or residue, from the beverage or from the vegetable preparation, and
   in a third step obtaining the so purified beverage or so purified vegetable preparation, wherein the lipophilic phase is selected from the group consisting of:
   fats;
   oils;
   waxes;
   paraffins;
   lipoids; and
   sterols.

2. The process according to claim 1, wherein the lipophilic phase is selected from the group consisting of:
   cocoa butter, coconut fat, neutral oils, sunflower oil, fractionated coconut oil, miglyol, stearins, yoyoba oil, beeswax, spermaceti, carnauba wax, and vaseline.

3. The process according to claim 2, wherein the lipophilic phase is selected from cocoa butter or miglyol.

4. A process for the removal of γ hexachloro cyclohexane contained in tea or Ginseng extract, said process comprising,
   (i) mixing tea or Ginseng extract with a lipophilic phase comprising cocoa butter to an extent effective to dissolve the γ hexachloro cyclohexane in the lipophilic phase; and
   (ii) separating the lipophilic phase containing γ hexachloro cyclohexane resulting from step (i) from the tea or Ginseng extract using a propylene membrane.

5. A process for the removal of at least one undesired lipophilic contamination or residue, which is contained in beverages or in vegetable preparations, comprising:
   in a first step mixing the beverage or the vegetable preparation with a lipophilic phase to dissolve and concentrate therein nearly quantitatively the contamination or residue, and wherein the lipophilic phase is of animal, vegetable, mineralic or synthetic origin, and is not toxic, not easily inflammable, not explosive and not volatile,
   in a second step separating the lipophilic phase, which contains the at least one contamination or residue, from the beverage or from the vegetable preparation, and
   in a third step obtaining the so purified beverage or so purified vegetable preparation, wherein in the second step the separation is conducted by phase separation of 2 liquid phases by membrane-separation using a polypropylene or teflon membrane with pore sizes in the range from 0.1 to 0.3 micrometer.

* * * * *